United States Patent [19]

Jackson

[11] Patent Number: 5,330,439
[45] Date of Patent: Jul. 19, 1994

[54] SAFETY DEVICE FOR USE IN COLLECTING FLUID SAMPLES

[75] Inventor: Craig M. Jackson, Del Mar, Calif.

[73] Assignee: American National Red Cross, Washington, D.C.

[21] Appl. No.: 865,374

[22] Filed: Apr. 8, 1992

[51] Int. Cl.$^5$ .............................................. A61M 5/32
[52] U.S. Cl. ................................... 604/192; 604/263; 211/74
[58] Field of Search ..................... 604/192, 263, 110; 128/763, 764, 919, 760, 762; 206/364–366, 443; 422/104, 58; 211/74

[56] References Cited

U.S. PATENT DOCUMENTS

| | | |
|---|---|---|
| 3,401,695 | 9/1968 | Rosenberg et al. . |
| 3,616,789 | 11/1971 | Grabhorn ............................ 128/762 |
| 3,633,566 | 1/1972 | Grabhorn ............................ 128/762 |
| 3,904,033 | 9/1975 | Haerr . |
| 3,905,772 | 9/1975 | Hartnett et al. ................. 211/74 X |
| 4,485,918 | 12/1984 | Mayer . |
| 4,559,042 | 12/1985 | Votel . |
| 4,573,975 | 3/1986 | Frist et al. . |
| 4,596,562 | 6/1986 | Vernon . |
| 4,610,667 | 9/1986 | Pedicano et al. . |
| 4,629,453 | 12/1986 | Cooper . |
| 4,654,034 | 3/1987 | Masters et al. . |
| 4,659,330 | 4/1987 | Nelson et al. . |
| 4,664,259 | 5/1987 | Landis . |
| 4,840,272 | 6/1989 | Goldman . |
| 4,840,618 | 6/1989 | Marvel ................................ 604/187 |
| 4,932,418 | 6/1990 | Coburn ................................ 128/764 |
| 4,982,850 | 1/1991 | Mears ................................... 211/74 |
| 5,127,531 | 7/1992 | Onodera ............................... 211/74 |
| 5,148,919 | 9/1992 | Rubin .................................. 206/443 |

Primary Examiner—John D. Yasko
Assistant Examiner—Vanitha Alexander
Attorney, Agent, or Firm—Harness, Dickey & Pierce

[57] ABSTRACT

A safety device for collecting fluids for laboratory testing is disclosed. More particularly, the invention relates to an apparatus for collecting multiple undiluted blood samples for subsequent laboratory testing wherein the apparatus is provided with a safety overshield which precludes the individual taking the blood sample from sustaining a needle stick injury. The apparatus includes a vacutainer tube retainer to which a safety overshield is attached. The safety overshield has an upwardly projecting peripheral rim which prevents the depositing needle from sliding off the face of the overshield and contacting the hand of the individual holding the vacutainer tube retainer.

22 Claims, 3 Drawing Sheets

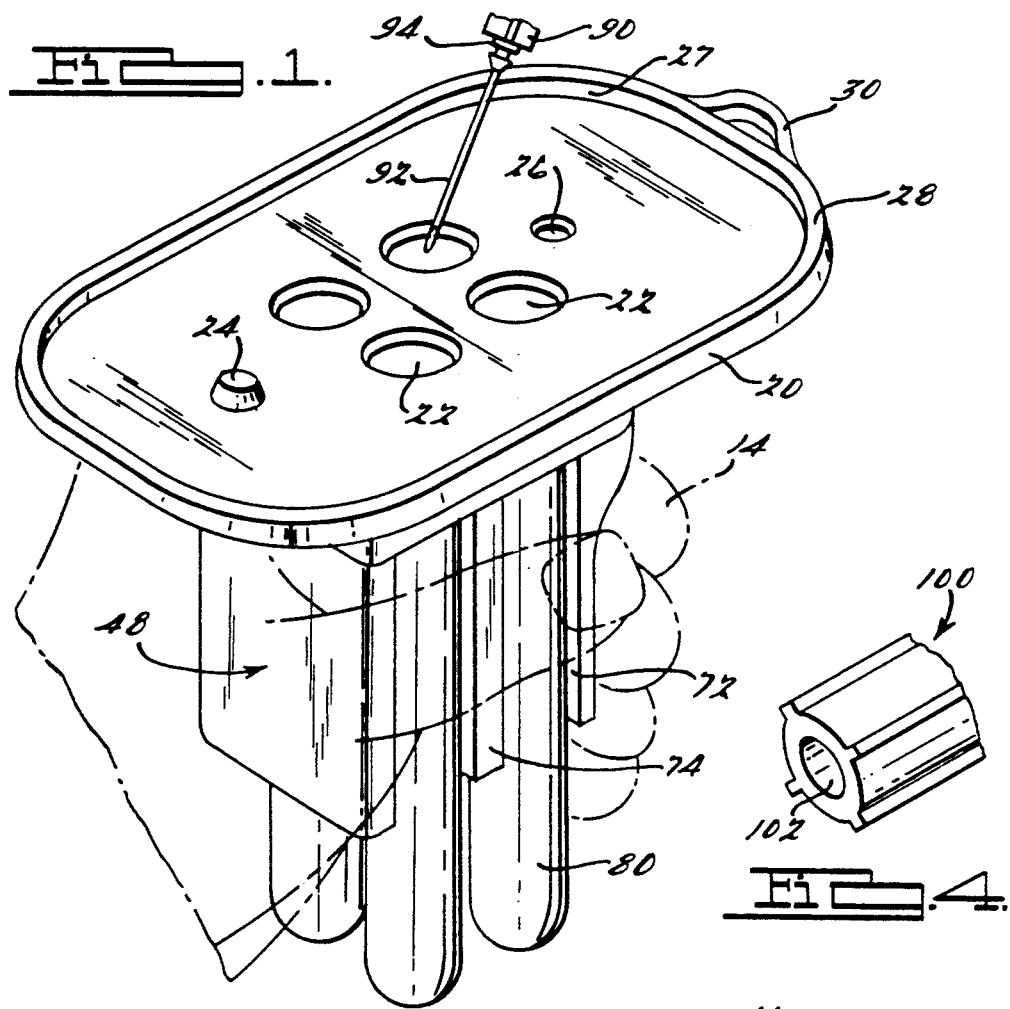
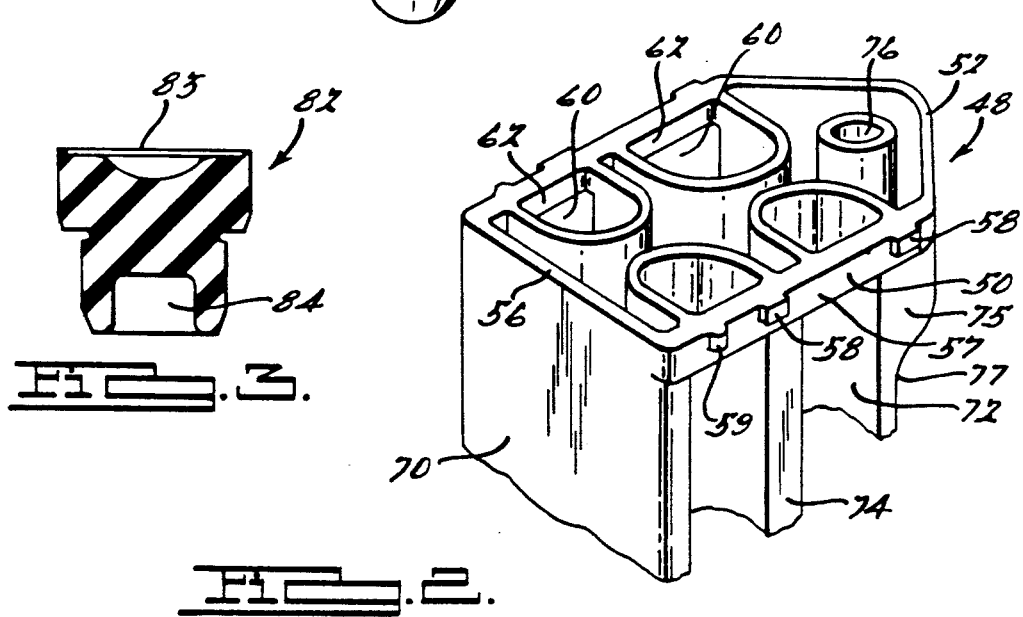

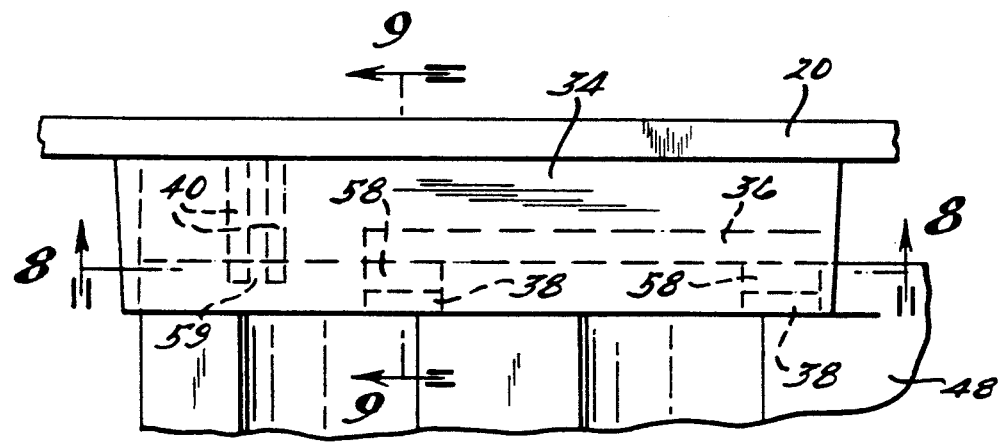
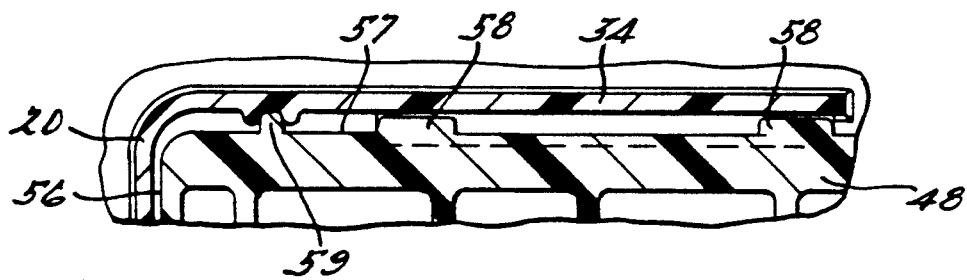
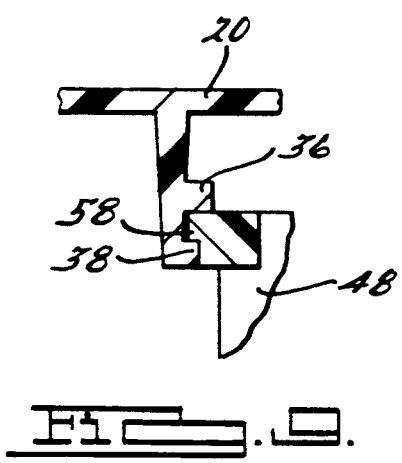
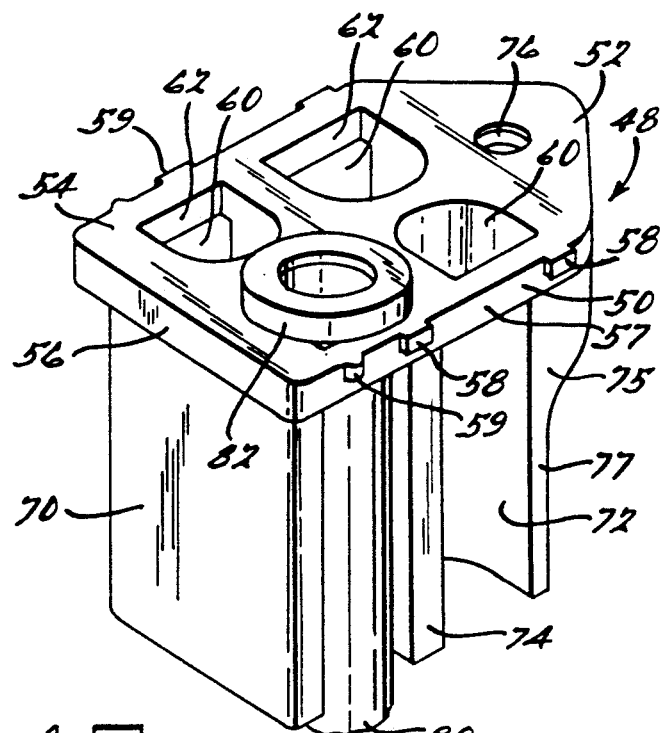

SAFETY DEVICE FOR USE IN COLLECTING FLUID SAMPLES

BACKGROUND OF THE INVENTION

1. Field of the Invention

This invention relates to a safety device for collecting fluids for laboratory testing and, more particularly, to a safety device for collecting undiluted and uncontaminated blood samples for laboratory testing.

2. Discussion of the Invention

The use of hypodermic needles in collecting fluids and more particularly, blood samples, presents a danger of accidental needle sticks to anyone exposed to such needles. This is especially true for the individual taking the fluid or blood sample. After use, the hypodermic needle could be contaminated with a variety of disease-causing agents such as Hepatitis B virus or HIV, the virus which leads to Acquired Immune Deficiency Syndrome (AIDS). These and other diseases can be transmitted to any person who is poked by a disease contaminated needle. Due to the hectic conditions often present in hospitals, one or more needles can often be found lying about in the presence of patients, blood donors and hospital personnel. Almost daily, reports of accidental needle stick injuries are communicated to the general public. Many times hospital personnel are required to have blood tests run after being punctured by an exposed, previously used needle in which case the costs of these tests are believed to be passed off onto hospital patients in the form of increased medical bills. Therefore, it is desirable to minimize the dangers associated with needle stick injuries by eliminating the exposure to contaminated needles.

Often needle stick injuries occur when a nurse, medical technician or phlebotomist attempts to collect multiple samples of blood in separate sterile vials, such as "Vacutainer®", which is a federally registered trademark of the Becton Dickinson Co., or "Monojet®", which is a federally registered trademark of Sherwood Medical Industries, blood collection tubings. Multiple samples are often necessary when various tests are to be run or when confirmation tests are required. To eliminate patient discomfort from multiple needle sticks, it is desirable to collect a sufficient amount of blood with a single insertion of a phlebotomy needle.

Vacutainer® tubings, which are evacuated tubings having needle penetrable stoppers inserted therein, are used to collect the blood samples and prevent the blood samples from becoming contaminated. Typically, when blood is to be collected directly from the patient or blood donor some type of flexible tubing having two juxtaposed hollow needles attached thereto is utilized. Located at one end of this tubing is the phlebotomy needle which is inserted into the individual to draw blood and at a second end is the depositing needle used to penetrate the stopper and deposit blood in the vacutainer tubings. Alternatively, when blood samples are collected into vacutainer tubings from a blood donor bag the flexible tubing usually only has one hollow needle which is attached at the depositing end. Regardless of whether the blood is collected directly from the patient or donor or is being transferred from a blood donor bag the depositing needle must be withdrawn and inserted into multiple numbers of stopper sealed tubings in order to collect multiple samples of blood. This repeated transfer of the depositing needle between fluid collection tubings creates multiple opportunities for needle stick injuries to occur. Therefore, it is desirable to minimize the danger of spreading diseases from the patient to the medical professional by precluding the incidence of needle stick injuries during blood sample collection.

Various patents have issued for devices which protect medical professionals from needle stick injuries. For example, U.S. Pat. No. 4,573,975 to First et al., discloses a protective shield surrounding a container for a hypodermic needle. Another patent, U.S. Pat. No. 4,670,667 to Pedicano et al., discloses a disposable safety needle sheath which has a funnel shaped entrance to protect the user's hand and guide the needle into the sleeve. There remains, however, a need for an improved safety device such as that of the present invention.

SUMMARY AND OBJECTS OF THE INVENTION

It is, therefore, the primary object of the present invention to provide a safety device which protects the user's hand from needle stick injuries while collecting multiple undiluted blood samples from a patient or blood donor or while back filling from tubing connected to a blood bag.

It is a further object of the present invention to provide a safety overshield which holds the fluid collection tubings in place during withdrawal of the depositing needle from the fluid collection tubing.

It is a further object of the present invention to provide a safety overshield which is capable of securing both a depositing needle and a phlebotomy needle after use.

It is a further object of the present invention to provide a fluid collection tube retainer which is capable of holding multiple tubes of varying sizes.

It is yet another object of the present invention to provide a fluid collection tube retainer which has an open construction.

It is yet another object of the present invention to provide a safety device which can be attached to a blood donor bag for ease of transport.

It is yet another object of the present invention to provide a reusable safety overshield and retainer.

The present invention, therefore, relates a safety device for preventing needle stick injuries while collecting blood samples. The device is used in association with a standard blood drawing tubing having two juxtaposed needle elements, one used to draw blood and the other used to transfer the drawn blood into multiple fluid collection tubings. Alternatively the safety device can be used with a standard blood transferring tubing which is attached at one end to a blood donor bag. The needle at the transfer end of the tubing, referred to herein as the depositing needle, is inserted through a stopper element which seals the fluid collection tube. To prevent the depositing needle from contacting the medical professional's hand if the depositing needle is misdirected during insertion through the stopper element, a safety overshield is positioned over the top of the fluid collection tubes and securely attached to the fluid collection tube retainer. The safety overshield generally is sufficient in area to cover the medical professional's hand while grasping the fluid collection tube retainer and is provided with an upwardly extending peripheral rim which helps to prevent the depositing needle from sliding off the face of the overshield if the needle is misdirected.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 1 is a perspective view of the present invention in an assembled arrangement with the depositing needle positioned to engage a fluid collection tube.

FIG. 2 is a perspective view of a fluid collection tube retainer of the present invention.

FIG. 3 is a side view in cross section of a stopper member.

FIG. 4 is a perspective view of a sheathing member which can be used to house either a phlebotomy needle or a depositing needle during nonuse.

FIG. 7 is a side view of the present invention showing a safety overshield attached to a fluid collection tube retainer.

FIG. 8 is a partially cut-away top view of the present invention showing a safety overshield attached to a fluid collection tube retainer.

FIG. 9 is an end view of the present invention partially in cross-section showing a safety overshield attached to a fluid collection tube retainer.

FIG. 10 is a perspective view of a second embodiment of a collection tube retainer according to the present invention.

DETAILED DESCRIPTION OF THE PREFERRED EMBODIMENTS

Figure 5:
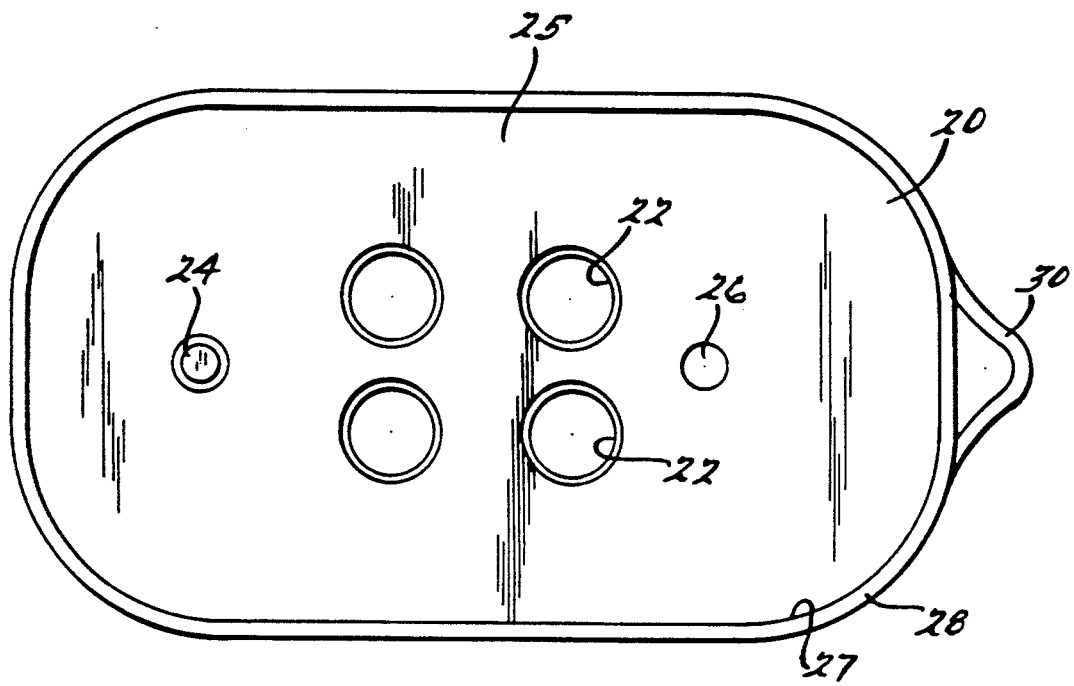
FIG. 5 is a top view of the safety overshield of the present invention.

Referring to FIG. 1 a perspective view of the safety device of the present invention is shown in an assembled arrangement. Typically a standard blood drawing tubing having two juxtaposed needle elements, one used to draw blood and the other used to transfer the drawn blood is used in association with the present invention when blood is being collected directly from the patient or donor. Alternatively, if the blood samples are being collected from a previously filled donor bag, the blood drawing tubing may be directly attached to the bag at one end and have a depositing needle extending from the other end. The safety device comprises a safety overshield 20 which is attachable to the top of a fluid collection tube retainer 48 having one or more fluid collection tubes 80 retained therein. The safety overshield 20 is designed to cover and protect the medical professional's hand and lower arm from a needle stick injury while taking fluid samples such as blood directly from a patient or blood donor. Both the safety overshield 20 and the fluid collection tube retainer 48 are preferably formed of a heavy duty transparent recyclable plastic material, such as the polycarbonate based plastic, Lexan ® which is a federally registered trademark of the General Electric Company.

Turning to FIG. 2 a perspective view of the fluid collection tube retainer 48 is shown with a single fluid collection tube 80 engaged within the fluid collection tube retainer 48. The fluid collection tube retainer 48 is typically comprised of a frame 50 located at the top and a downwardly extending body portion 70. The frame 50 has an approximate pentagonal shape wherein the leading end 52 has the tapered appearance of an isosceles triangle. Alternatively, as shown in the embodiment of FIG. 10, the frame 50 is provided with a face 54 having a relatively flat surface. Alternatively, as shown in the embodiment of FIG. 2, the face of the frame 50 can be eliminated which results in a relatively open design and reduces the amount of plastic required to form the safety device of the present invention. This open frame 50 design tends to allow cleaning solvents such as bleach to readily contact all surfaces during sterilization and decontamination of the fluid collection tube retainer.

Frame 50 is provided with four openings 60 through which the fluid collection tubes, also known in the medical profession as Vacutaimer ® tubes, are initially inserted. In light of the fact that varying amounts of blood are required for different types of laboratory analysis, the openings 60 have been designed such that different sized fluid collection tube 80 may be utilized with the present invention. Accordingly, three of these openings 60 are sized to accommodate fluid collection tubes which are approximately 1.2 centimeters in diameter and a fourth opening is designed to host a fluid collection tube which is approximately 1.6 centimeters in diameter. Although fluid collection tubes 80 having diameters of 1.2 and 1.6 centimeters are generally the most common sizes used for collecting blood samples, it will be appreciated that the fluid collection tube retainer can be formed to host various sized fluid collection tubes.

When viewing the fluid collection tube retainer 48 from the top each of these openings 60 appear to be U-shaped having a straight edge 62 where they extend inward from the frame 50. This straight edge 62 in conjunction with the round nature of the fluid collection tubes 80 typically allows each fluid collection tube 80 to be provided with a detachable bar code label (not shown) without risk of losing or damaging the label during insertion of the fluid collection tube. Also provided as part of the frame 50 is an aperture 76 located at the leading end 52. Aperture 76 serves as a host position for the phlebotomy needle (not shown) and protective sheath of FIG. 4 when the needle is not being utilized or after it has been used and resheathed.

The body portion 70 of the fluid collection tube retainer 48 is designed to fit within the hand 12 of the medical professional, as demonstrated in phantom on FIG. 1. The body portion 70 contains four concave grooves 72 which host the middle sections of the fully inserted fluid collection tubes 80. Each of these grooves 72 extend downward for the length of the body portion 70 contiguously from the corresponding opening 60. Separating each of these grooves 72 is partition 74 which prevents the fluid collection tubes 80 from coming in contact with each other during use. As a result of preventing the fluid collection tubes 80 from contacting each other in this manner, the risk of breaking one or more of them during the blood collection process is greatly reduced.

The leading end of the collection tube retainers body portion 70 is specifically provided with a downwardly fluted projecting portion 75 to accommodate varying hand sizes. For example, if the medical professional utilizing the safety device has a relatively small hand, the medical professionals' first finger 14 naturally comes to rest at the base of the projection 75 as the fluid collection tube retainer 48 is initially grasped. This projecting portion 75 would then screen the first finger 14 thereby affording the medical professional utilizing the safety device additional protection against needle stick injuries. Alternatively, if the medical professional's hand is relatively large the medical professional's first finger would more naturally come to rest over the downwardly fluted projecting portion 75.

An aperture 76 found at the leading end 52 of frame 50 is provided through the downwardly fluted projecting portion 75 in both the embodiment of FIG. 2 and the embodiment of FIG. 10 which can be used to host the resheathed depositing needle 92 during nonuse. At approximately the halfway point on the leading end 52 of the fluid collection tube retainer's body portion, the downwardly fluted projecting portion 75 merges into the front wall 77 of the fluid collection tube retainer 48. At this point, the aperture 76 in the fluted portion 75 ceases.

Referring to FIG. 5, a top view of the safety overshield 20 of the present invention is shown. The safety overshield 20 which has a surface area approximately twice as large as that of the fluid collection tube retainer frame 50 is shown here to have a rectangular shape with rounded corners. Although the rectangular configuration is believed to approximate the shape of a hand while grasping the fluid collection tube retainer, it will be appreciated that the safety overshield can have many other configurations. Safety overshield 20 is provided with four apertures 22 which are spaced apart so as to be in axial alignment with the openings 60 contained on the frame 50. To assist in guiding the depositing needle 92 into and through stoppers 82, the apertures 22 taper downward to guide the needle 92 toward the center 83 of the stopper 82.

Another aperture 26 through which the resheathed phlebotomy needle 92 can be inserted during nonuse is also provided on the safety overshield 20. This aperture 26 is axially aligned with the aperture 76 found at the leading end of the fluid collection tube retainer 48 such that the phlebotomy needle 92 can be inserted through the overshield aperture 26 and the collection tube retainer aperture 76. At the trailing end of the safety overshield 20 an upwardly projecting boss 24 is provided which serves as a host position for a stopper member 82.

An upwardly projecting peripheral rim 28 which helps preclude the depositing needle 92 from contacting the medical professionals' hand during insertion and withdrawal of the depositing needle from the fluid collection tubes 80 is also provided on safety overshield 20. In the event that the medical professional misdirects the depositing needle during insertion or withdrawal into the fluid collection tube 80, the inner wall 27 of this upwardly projecting peripheral rim 28 catches the depositing needle 92 and keeps it on the face 24 of the safety overshield 20. Extending from the peripheral rim at the leading end of the safety overshield 20 is a loop 30 member which allows the safety overshield to be connected to a blood donor bag (not shown).

Figure 6:
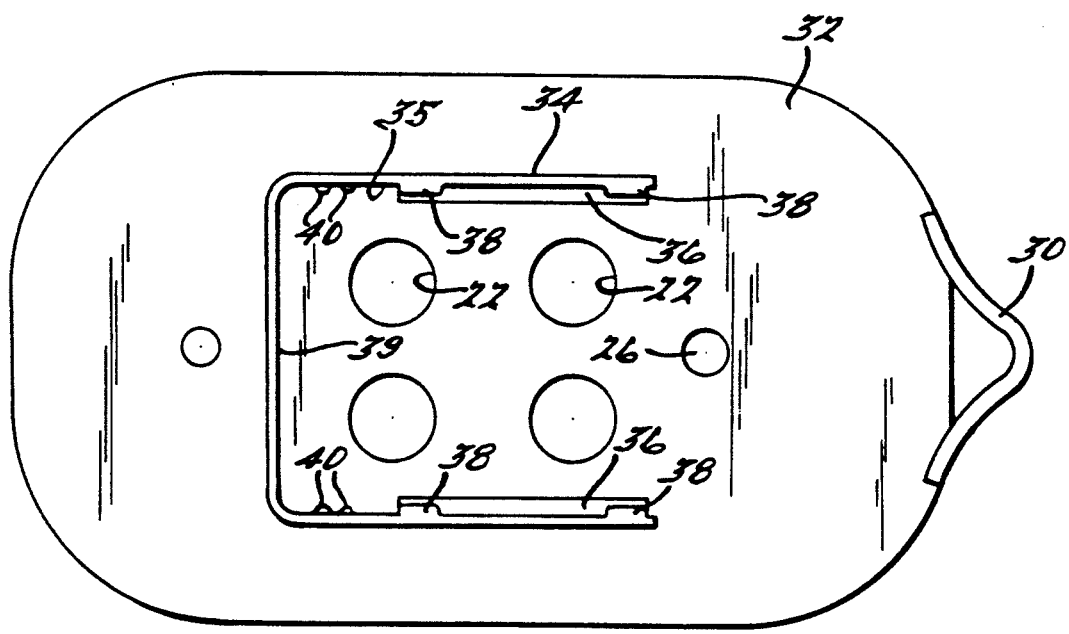
FIG. 6 is a bottom view of the safety overshield of the present invention.

Referring to FIGS. 6-9, means of connecting the safety overshield 20 to the frame 50 of the collection tube retainer 48 are shown. FIG. 6 is a bottom view of the safety overshield 20 showing that the bottom face 32 is provided with an extending lip 34 which surrounds the rear edge 56 and two side edges 57 of the frame 50. The two inner walls 35 of the extending lip 34 are provided with a long horizontal flange 36 occurring approximately midway on the inner walls 35. Below each horizontal flange 36 is a pair of inwardly projecting post members 38. Also appearing on each inner sidewall near the rear wall 39 is a pair of vertically extending nubs 40 which interconnect with the outwardly projecting post members 59 contained on the side edges 57 of the frame 50. Upon fully connecting and attaching the safety overshield 20 to the retainer 48 the projecting bars 58 extending from the side edges 57 are positioned contiguously between the horizontal flange 36 and the projecting post members 38. Under this arrangement the projecting bars 58 are in a stacked relationship with the post members.

To utilize the present invention, a medical professional grasps the fluid collection tube retainer 48 with one hand and inserts the fluid collection tubes 80 with the other. The evacuated fluid collection tubes 80, capped with detachable needle penetrable stoppers 82, are inserted through the various openings 60 contained on the frame 50. The fluid collection tubes 80 pass through openings 60 to engage grooves 72 contained on the fluid collection tube retainer 48. Upon complete insertion of the fluid collection tubes 80, the bottom edge of each stopper 82 is in direct contact with the frame 50. The open nature of the fluid collection tube retainers body portion 70 allows the medical professional to tacitly confirm that each of the fluid collection tubes 80 are properly in position to collect the blood samples and insures that the bar code labels and numbers are completely visible.

Once the fluid collection tubes 80 are in place, the safety overshield 20 is connected to the fluid collection tube retainer 48 as shown in FIGS. 7-9. Initially the safety overshield 20 is either placed on top of the frame 50 such that the bottom edges of the horizontal flanges 36 come to rest upon the two longest sides of frame 50 or is slid onto the frame from behind. The safety overshield 20 is then advanced forward until the two forward most outwardly projecting post members 38 located on the sides of the frame 50 are engaged between the horizontal flanges 36 and the two inwardly projecting post members 38 of the extending lip 34. The safety overshield 20 continues to be advanced forward until the rearward most post members 59 which project outwardly from the sides of the frame 50 are engaged by the vertical nubs 40 provided on the inner sidewalls 35 of the extending lip 34.

With the safety overshield 20 locked onto the fluid collection tube retainer 48 the medical professional may now collect the desired volume of blood by inserting the depositing needle 92 through the apertures 22 and stoppers 82 into the fluid collection tubes 80. Placement of sheath 100 locks safety overshield 20 onto fluid collection tube retainer 48. Due to the evacuated nature of the fluid collection tubes 80 blood is readily drawn into the tubes by suction until the transfer hose is clamped or pinched to preclude the flow.

After the blood samples have been collected it may be desirable to store the fluid transfer hose 90 until it can be disposed. To do so, the phlebotomy needle is withdrawn from the patient or blood donor and is resheathed with the plastic sheath 100 shown in FIG. 4. Resheathing occurs by slipping the sheath 100 over the end of either the phlebotomy needle or the depositing needle and sliding the needle into axial bore 102 until the top of sheath 100 engages the nipple 94 contained at the base of the needle. The resheathed phlebotomy needle is then inserted through the aperture 26 located on the leading end of safety overshield 20 and down into aperture 76 of the fluid collection tube retainer 48 such that the needle sheathing 100 is contained completely below the safety overshield 20. As a result of positioning the needle sheath 100 below the safety overshield 20 the phlebotomy needle can subsequently be withdrawn from aperture 76 for disposal but the needle sheath 100 remains intact within the fluid tube retainer 48 until the safety overshield 20 is removed.

Likewise, it may be desirable to store the depositing needle 92 during periods of nonuse. The safety overshield 20 has therefore been provided with an upwardly projecting boss 24 which is engaged by a stopper 82. As shown in FIG. 3, the stopper contains an aperture 84 on the bottom portion thereof which surrounds the projecting boss 24. Once the stopper 82 is secured upon safety overshield 20 by pressing the stopper 82 over the boss 24, the depositing needle 92 can then be inserted into the top of stopper 82 which retains the transfer hose 90 until it can be disposed of.

Now that the blood samples have been collected and the blood transfer hose 90 has been disposed of, the safety overshield 20 can be readily removed from the fluid collection tube retainer 48 by simply grasping the safety overshield 20 and sliding it in a rearward direction. This device can be decontaminated by either washing or autoclaving and reused almost indefinitely. If irreparable damage occurs to the device the plastic (Lexan ®) can be recycled by remelting and remolding into new shields by the manufacturers. Thus this device need not contribute to accumulating medical waste.

I claim:

1. A safety device for use in collecting fluids into fluid collection tubes having penetrable stopper means inserted therein through a fluid transfer hose having at least one hollow needle attached thereto comprising:
   a fluid collection tube retainer, said retainer including a frame having a plurality of openings therethrough for receiving fluid collection tubes and one or more openings for receiving one end of a fluid transfer hose and a gripable body member having a plurality of grooves for partially engaging said fluid collection tubes; and
   a safety overshield selectively attached to said fluid collection tube retainer having a downwardly extending lip which engages said frame, a plurality of openings one the face of said safety overshield which correspond to the openings of said frame, and an upwardly projecting rim about the periphery of said safety overshield.

2. The safety device according to claim 1 wherein said fluid collection tube retainer has an open design which facilitates decontamination and sterilization with solvents.

3. The safety device according to claim 1 wherein said fluid collection tube retainer body has a downwardly tapering fluted first end.

4. The safety device according to claim 3 wherein said fluted first end has at least one aperture therethrough for securing a fluid transfer hose.

5. The safety device according to claim 1 wherein said fluid collection tube retainer has four openings in said frame for receiving said fluid collection tubes and four grooves in said body portion for limiting lateral movement of said fluid collection tubes, wherein each groove is contiguous with one of said openings.

6. The safety device according to claim 1 wherein each frame opening has at least one straight edge.

7. The safety device according to claim 1 wherein the outer periphery of said frame has a plurality of projecting bars, wherein each bar is engaged by said frame between a horizontal flange and a post member projecting inwardly from the safety overshield extending lip.

8. The safety device according to claim 1 adapted to retain at least one fluid collection tube in said collection tube retainer, wherein said fluid collection tube is retained by said fluid collection tube retainer, said fluid collection tube including penetrable stopper means extending upwardly from said tube such that the bottom side of said safety overshield abuts said penetrable stopper means to provide a fluid tight seal upon complete attachment of said overshield to said fluid collection tube retainer.

9. The safety device according to claim 8 wherein upon complete attachment of said safety overshield to said fluid collection tube retainer said safety overshield precludes said fluid collection tubes from being dislodged as the depositing needle of said fluid transfer hose is withdrawn from the tubes.

10. The safety device according to claim 1 wherein said safety overshield has means of attachment to a blood donor bag for use as a unit.

11. The safety device according to claim 1 wherein said safety overshield and said fluid collection tube retainer are made of a transparent material to allow viewing of said fluid collection tubes.

12. The safety device according to claim 11 wherein said transparent material comprises a polycarbonate based plastic.

13. An apparatus for preventing needle stick injuries while drawing blood for laboratory testing and depositing the blood into evacuated fluid collection tubes having stopper members inserted therein with a phlebotomy needle, comprising:
   a collection tube retainer having an upper peripheral frame and a body portion, wherein said upper peripheral frame has a plurality of openings for receiving said fluid collection tubes and at least one opening for securing said phlebotomy needle, said body portion including a plurality of vertical grooves for preventing lateral movement of said fluid collection tubes and at least one groove for securing a transfer hose; and
   overshield means comprising a selectively attached plate member having a plurality of openings corresponding to the openings in said frame for access to said fluid collection tubes, at least one opening for insertion of said phlebotomy needle, a downwardly extending lip which partially engages the periphery of said frame thereby attaching said plate to said retainer and an upwardly projecting rim about the periphery of said plate.

14. The apparatus for preventing needle stick injuries according to claim 13 wherein each of said openings contained on said collection tube retainer for receiving fluid collection tubes has at least one straight edge.

15. The apparatus for preventing needle stick injuries according to claim 13 wherein said overshield means extending lip contains a plurality of slots which are engaged by bars projecting outwardly from the periphery of said frame which secure said overshield means to said fluid collection tube retainer.

16. The apparatus for preventing needle stick injuries according to claim 13 wherein said fluid collection tube retainer body has a fluted front end which tapers downward, said fluted front end having an aperture therethrough for securing said phlebotomy needle during non-use.

17. A method of preventing a needle stick injury while collecting fluid samples, comprising the steps of:
  (a) providing one or more fluid collection tubes wherein said tubes have needle penetrable stoppers inserted therein;
  (b) providing at least one fluid transfer hose having first and second hollow needles attached thereto at opposite ends;
  (c) providing a two-piece safety device, said device including:
    a fluid collection tube retainer having openings which house said fluid collection tubes and at least one opening for maintaining said fluid transfer hose; and
    a safety overshield attachable to said fluid collection tube retainer, wherein said safety overshield has a plurality of openings which correspond to the openings on said fluid collection tube retainer and an upwardly projecting rim about the periphery;
  (d) inserting said fluid collection tubes into said fluid collection tube retainer;
  (e) attaching said safety overshield to said fluid collection tube retainer;
  (f) drawing fluid into said fluid transfer hose through said first needle;
  (g) inserting said second needle into a fluid collection tube through an opening in said safety overshield and through said penetrable stopper;
  (h) filling said fluid collection tube;
  (i) withdrawing said second needle from said fluid collection tube and storing said needle within the opening for maintaining said fluid transfer hose.

18. A method of collecting fluid samples using a transfer hose having hollow needles attached at both ends, said method comprising the steps of:
  (a) providing means for collecting said fluid samples, said means having needle penetrable stoppers inserted therein;
  (b) providing means for preventing needle stick injuries, said means including:
    a fluid collection tube retainer having a plurality of openings from which said means for collecting said fluid samples extend; and
    an overshield attachable to said fluid collection tube retainer, wherein said overshield has a plurality of openings and an upwardly projecting peripheral rim;
  (c) inserting said means for collecting fluid samples into said fluid collection tube retainer;
  (d) attaching said overshield to said retainer;
  (e) inserting one of said hollow needles into a fluid collection tube through an opening in said overshield and through said penetrable stopper;
  whereby said fluid may now be deposited and collected for laboratory testing.

19. The safety device according to claim 1 wherein said safety overshield further comprises at least one boss projecting upwardly from said face.

20. The safety device according to claim 19 wherein said boss includes stopper means for receiving the hollow needle during periods of nonuse.

21. The safety device according to claim 13 wherein said overshield means further comprises at least one boss projecting upwardly from said plate member.

22. The safety device according to claim 21 wherein said boss includes stopper means for receiving the phlebotomy needle during periods of nonuse.

* * * * *